(12) United States Patent
Quan et al.

(10) Patent No.: US 11,890,298 B2
(45) Date of Patent: Feb. 6, 2024

(54) FUCOIDAN HAIR GROWTH AGENT

(71) Applicant: COSMED PHARMACEUTICAL CO., LTD., Kyoto (JP)

(72) Inventors: Ying-shu Quan, Kyoto (JP); Hirofumi Yamashita, Kyoto (JP); Fumio Kamiyama, Kyoto (JP); Akira Yamamoto, Kyoto (JP); Hidemasa Katsumi, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 151 days.

(21) Appl. No.: 17/498,197

(22) Filed: Oct. 11, 2021

(65) Prior Publication Data

US 2022/0023184 A1 Jan. 27, 2022

Related U.S. Application Data

(62) Division of application No. 16/084,166, filed as application No. PCT/JP2017/010571 on Mar. 16, 2017, now abandoned.

(30) Foreign Application Priority Data

Mar. 16, 2016 (JP) ................................ 2016-074691

(51) Int. Cl.
| | |
|---|---|
| *A61K 36/00* | (2006.01) |
| *A61K 31/737* | (2006.01) |
| *A61P 17/14* | (2006.01) |
| *A61K 9/06* | (2006.01) |
| *A61K 36/23* | (2006.01) |
| *A61K 36/9068* | (2006.01) |
| *A61M 37/00* | (2006.01) |

(52) U.S. Cl.
CPC .............. *A61K 31/737* (2013.01); *A61K 9/06* (2013.01); *A61K 36/23* (2013.01); *A61K 36/9068* (2013.01); *A61M 37/0015* (2013.01); *A61P 17/14* (2018.01); *A61M 2037/0023* (2013.01); *A61M 2037/0061* (2013.01)

(58) Field of Classification Search
None
See application file for complete search history.

(56) References Cited

U.S. PATENT DOCUMENTS

| | | | |
|---|---|---|---|
| 6,495,174 B1 | 12/2002 | Niazi | |
| 2003/0039670 A1* | 2/2003 | Mizutani | ................ A61Q 19/00 424/401 |
| 2006/0093566 A1 | 5/2006 | Mizutani et al. | |
| 2010/0030152 A1 | 2/2010 | Lee et al. | |
| 2014/0371713 A1 | 12/2014 | Quan et al. | |
| 2015/0025452 A1 | 1/2015 | Marinkovich et al. | |
| 2015/0125484 A1* | 5/2015 | Wang | ................... A61K 8/9794 424/195.15 |
| 2016/0001053 A1 | 1/2016 | Quan et al. | |
| 2021/0213265 A1 | 7/2021 | Quan et al. | |

FOREIGN PATENT DOCUMENTS

| | | |
|---|---|---|
| CN | 1433295 A | 7/2003 |
| CN | 101557848 A | 10/2009 |
| CN | 105232577 A | 1/2016 |
| EP | 1 234 568 A1 | 8/2002 |
| JP | 2003-155218 A | 5/2003 |
| JP | 2005-154321 A | 6/2005 |
| JP | 2005-281277 A | 10/2005 |
| JP | 2007-262036 A | 10/2007 |
| JP | 2008-169140 A | 7/2008 |
| JP | 2009-114170 A | 5/2009 |
| JP | 2014-218440 A | 11/2014 |
| JP | 2015-129101 A | 7/2015 |
| KR | 10-2002-0067041 A | 8/2002 |
| KR | 10-2002-0084718 A | 11/2002 |
| KR | 10-2014-0125364 A | 10/2014 |
| KR | 10-2015-0118136 A | 10/2015 |
| WO | WO-01/39731 A1 | 6/2001 |
| WO | WO-2012/128363 A1 | 9/2012 |

OTHER PUBLICATIONS

International Search Report for the Application No. PCT/JP2017/010571 dated Jun. 6, 2017.
Written Opinion of the International Searching Authority (PCT/ISA/237) for the Application No. PCT/JP2017/010571 dated Jun. 6, 2017.
Quan, Ying-shu, "Development of microneedle and application for antiwrinkle, whitening and hair growth", Fragrance Journal, 2015, vol. 43, No. 1, pp. 34-38.

(Continued)

*Primary Examiner* — Russell G Fiebig
(74) *Attorney, Agent, or Firm* — Cheng Law Group, PLLC

(57) ABSTRACT

To develop a novel administration method of a fucoidan-containing hair-growing agent and to provide a means for exerting excellent effects of a fucoidan.
A hair-growing agent of the present invention is characterized in that it is composed of a combination of a fucoidan-containing microneedle and a fucoidan-containing liniment. A base of the fucoidan-containing microneedle is preferably a biosoluble polymer. A hair-growing method of the present invention is characterized in that the fucoidan-containing microneedle and the fucoidan-containing liniment are concomitantly used.

6 Claims, 6 Drawing Sheets

(56) References Cited

OTHER PUBLICATIONS

McAllister, D. et al., "Microfabricated needles for transdermal delivery of macromolecules and nanoparticles: Fabrication methods and transport studies", Proceedings of the National Academy of Sciences, 2003, vol. 100, pp. 13755-13760.
Prausnitz, Mark R., "Microneedles for transdermal drug delivery", Advanced Drug Delivery Reviews, 2004, vol. 56, pp. 581-587.
Sachdeva, V. et al., "Microneedles and their Applications", Recent Patents on Drug Delivery & Formulation, 2011, vol. 5, pp. 95-132.
Supplementary European Search Report for the Application No. EP 17 766 763.1 dated Nov. 13, 2019.
Miao, Yong et al., "6-Gingerol Inhibits Hair Shaft Growth in Cultured Human Hair Follicles and Modulates Hair Growth in Mice", PLOS One, 2013, vol. 8, Issue 2, e57226, 6 pages.
Ines Nur Hendriani et al., "Uji Aktivitas Sediaan Hair Tonic Kombinasi Ekstrak Daun Pare (*Momordica charantia*) Dan Ekstrak Wortel (*Daucus carota* L.) Pada Kelinci Jantan New Zealand White", Medika Tadulako, Jurnal Iimiah Kedokteran, 2019, vol. 6, No. 2, pp. 140-147.
The First Office Action for the Application No. 201780016596.6 from The State Intellectual Property Office of the People's Republic of China dated Dec. 1, 2020.
Canadian Office Action for the Application No. 3,017,448 dated Mar. 27, 2023.
European Office Action for the Application No. 17 766 763.1 dated Sep. 30, 2022.
Australian Examination Report No. 1 for the Application No. 2017232597 dated Oct. 20, 2021.
Korean Office Action for the Application No. 10-2018-7026474 dated Oct. 29, 2021.
Han, Mee-Ree et al., "Characteristics and Hair Growth Efficacy of Water Dissolving Micro-needles Containing Minoxidil Regarding Length of Micro-needles", College of BioNano Technology and Gachon BioNano Research Institute, Gachon University, Polymer(Korea), 2013, vol. 37, No. 3, pp. 393-398.
Korean Office Action for Application No. 10-2018-7026474 dated Dec. 12, 2022.

* cited by examiner

[FIG. 1]
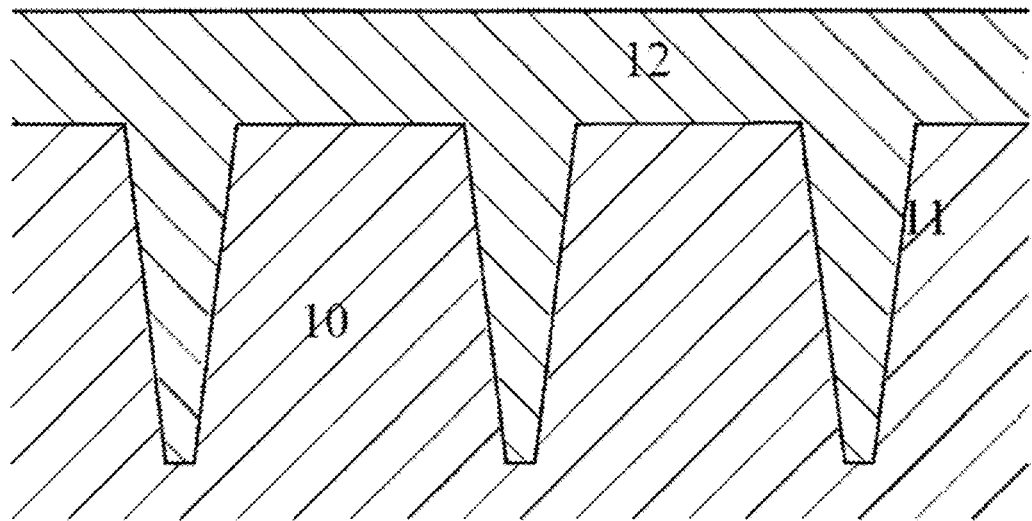
[FIG. 2]
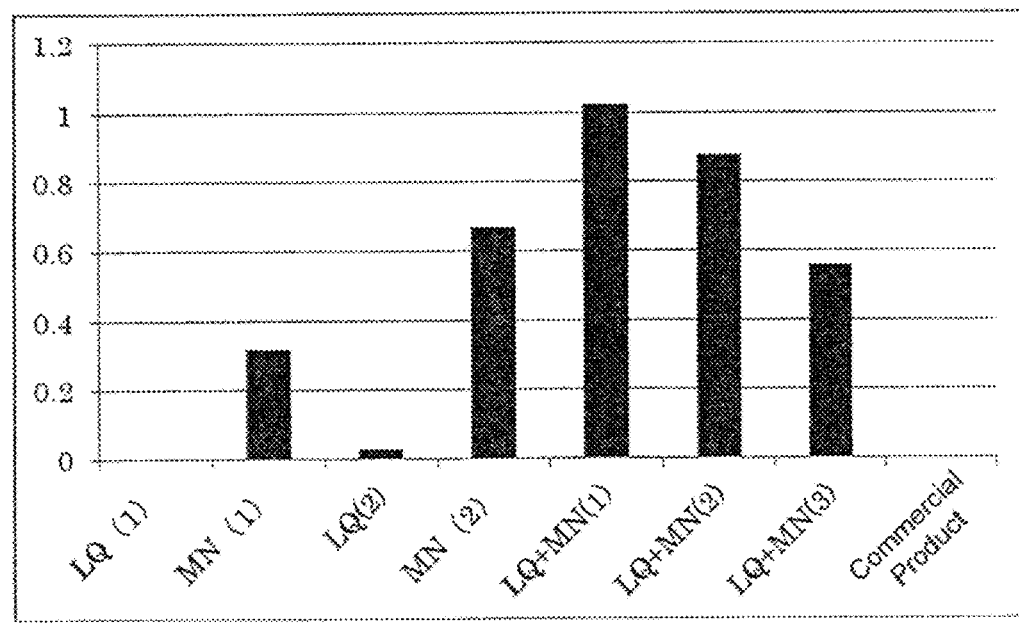

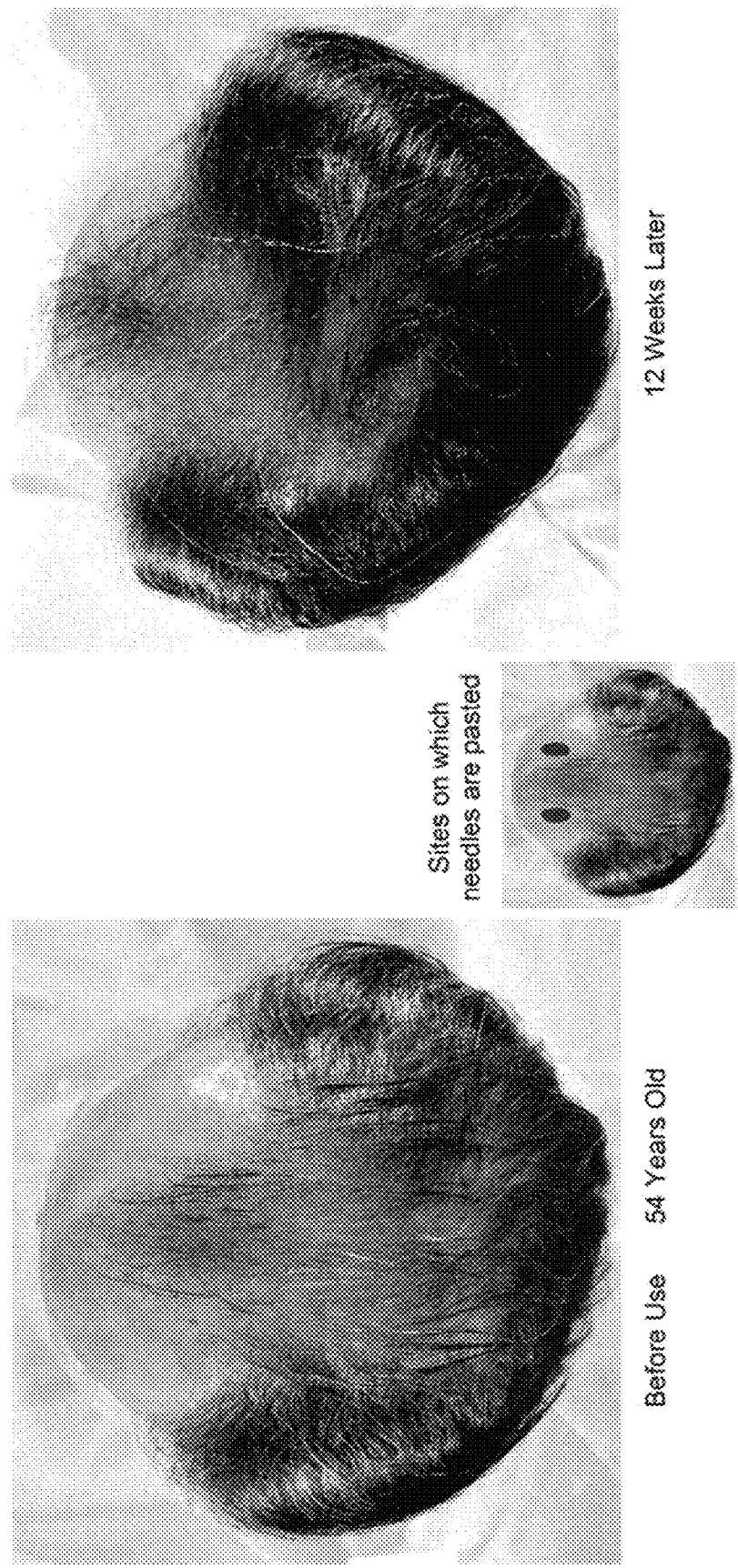
[FIG. 3A]

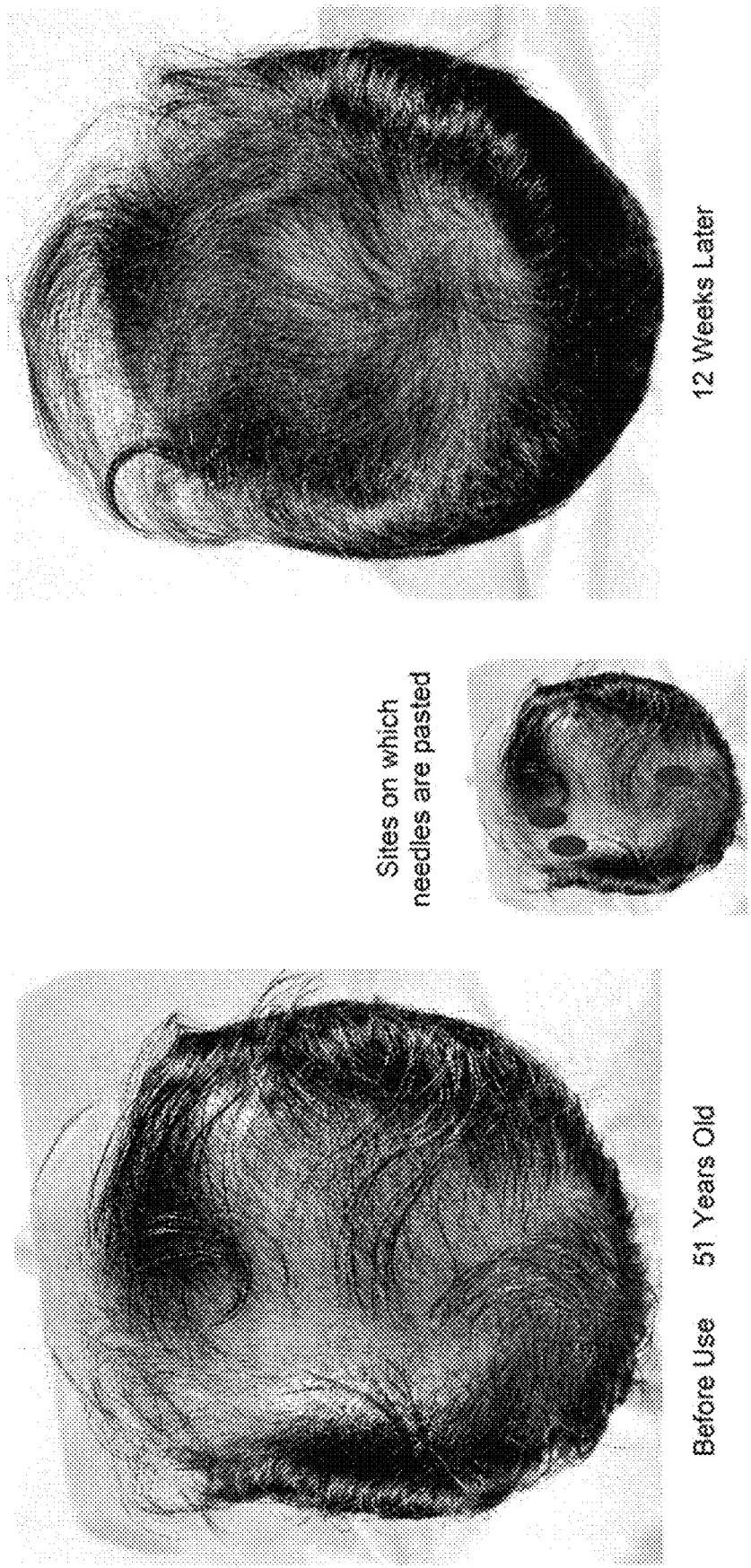
[FIG. 3B]

[FIG. 4]
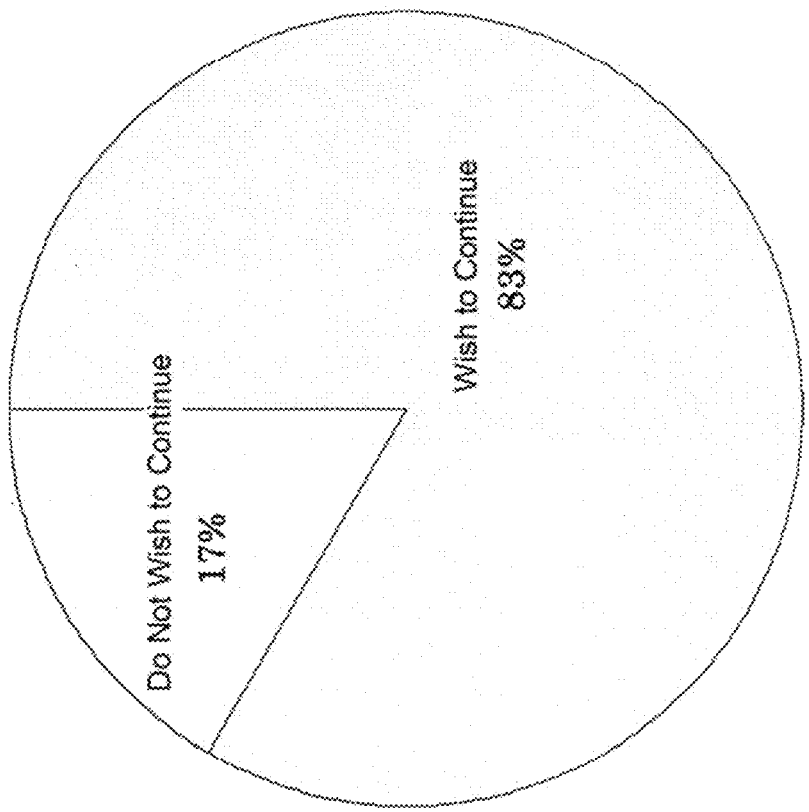
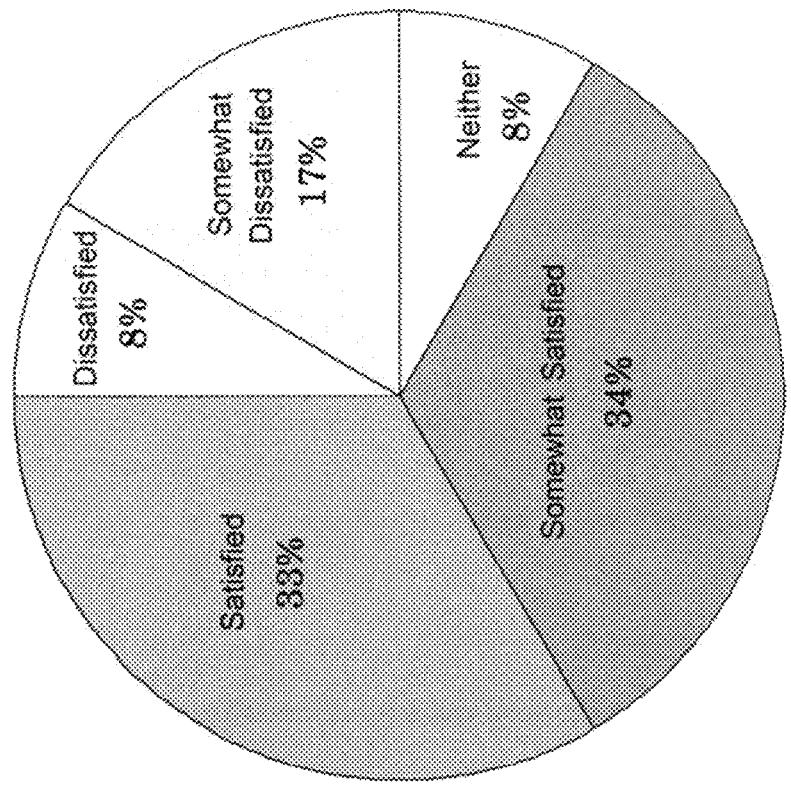

[FIG. 5]
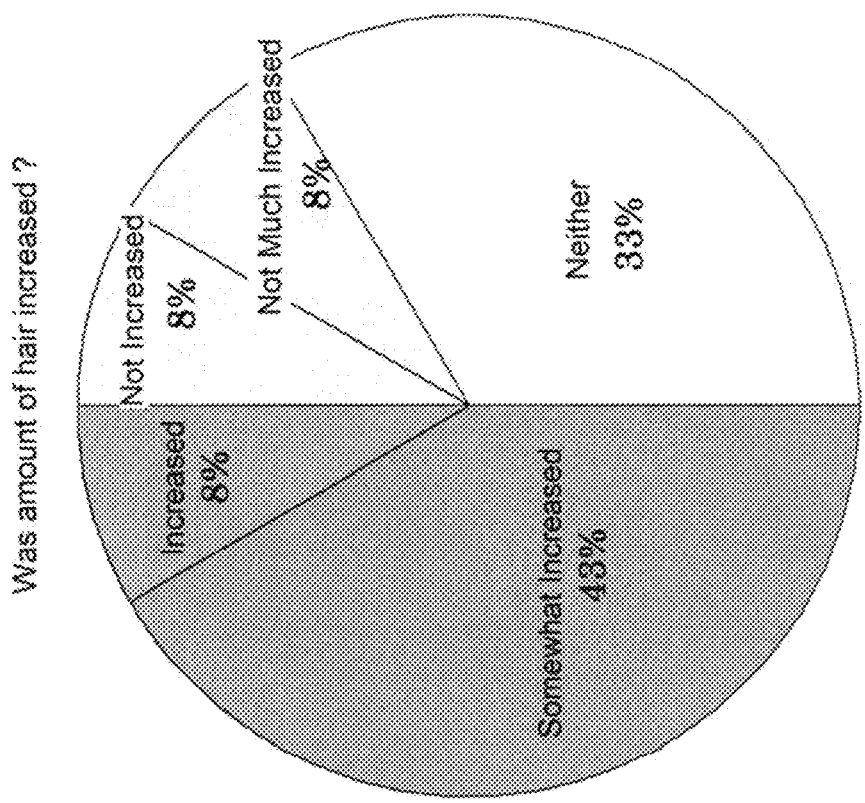
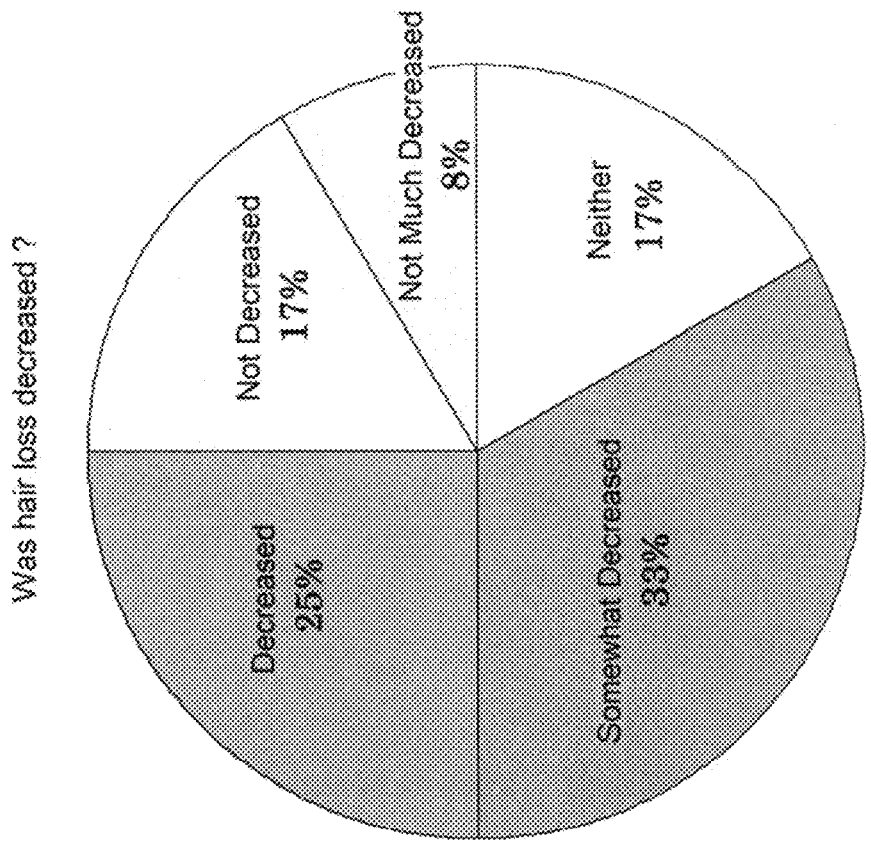

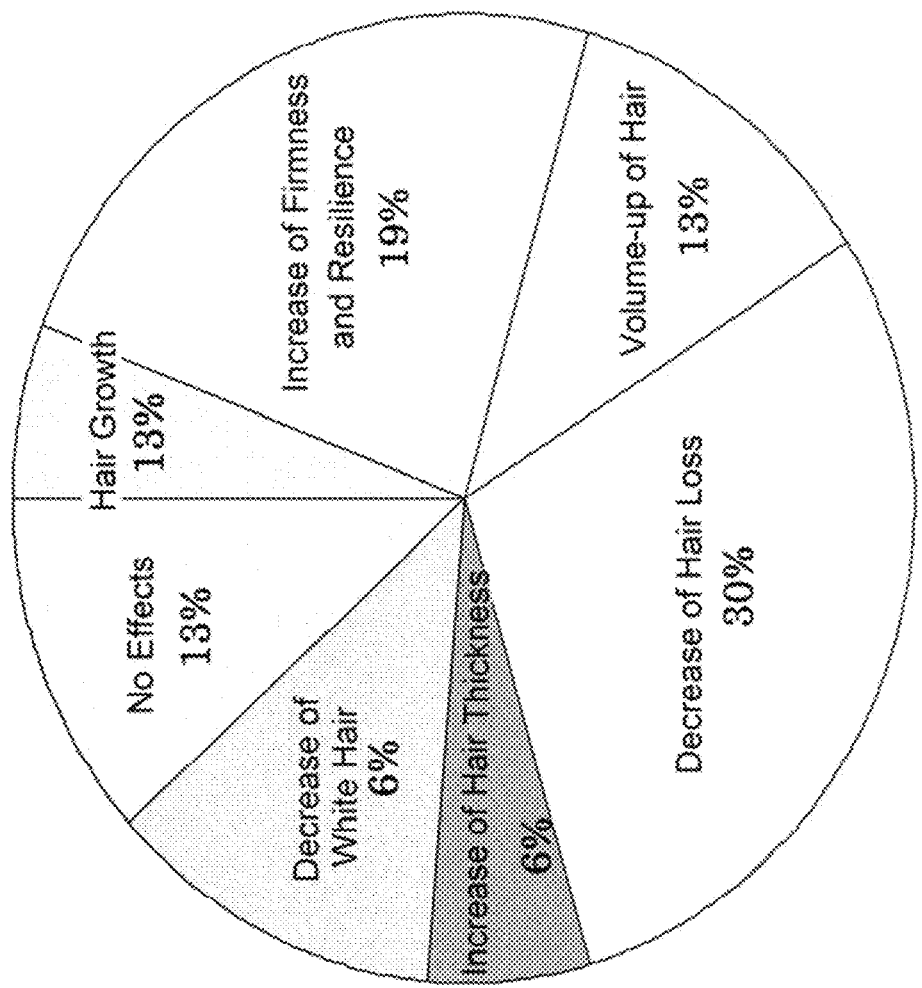

FUCOIDAN HAIR GROWTH AGENT

CROSS-REFERENCE TO RELATED APPLICATIONS

This application is a Divisional Application of patent application Ser. No. 16/084,166 filed on Sep. 11, 2018, which is a 371 application of Application Serial No. PCT/JP2017/010571, filed on Mar. 16, 2017, which is based on Japanese Patent Application No. 2016-074691, filed on Mar. 16, 2016, the entire contents of which are hereby incorporated by reference.

TECHNICAL FIELD

The present invention relates to a hair-growing agent composed mainly of fucoidan.

BACKGROUND ART

Fucoidan is a kind of acidic polysaccharide polymers containing fucose sulfate as a main constituent sugar. Fucoidan is a viscous component contained in brown algae such as *Undaria pinnatifida, Cladosiphon okamuranus* and tangle weed, and is known to have a hair-growing effect.

In relation to the hair-growing effect of fucoidan, a hair-growing composition containing fucoidan (Patent Document 1), a cosmetic containing fucoidan or a decomposed product thereof and having a hair-growing effect (Patent Document 2), foods and drinks containing fucoidan and having a hair-growing effect (Patent Document 3), a fact that a high-molecular-weight fucoidan having an average molecular weight of 1,000,000 or more is relatively effective for hair growth (Patent Document 4), an oral hair-growing agent with a combination of fucoidan and a seaweed-derived protein (Patent Document 5), a hair-growing agent containing fucoidan and a soybean protein (Patent Document 6), a hair-repairing agent obtained by blending propolis and the like into fucoidan (Patent Document 7) have already been published. All of them are oral agents or liniments.

However, it is well known that even if a drug is orally administered, the drug is not necessarily delivered to a site of a body where an effect of the drug is expected to be exerted, and the utilization rate of the oral drug is low in many cases. Also, it is well known that even if the drug is applied to a particular site of the body, a corneum acts as a barrier to drug penetration, and the drug does not sufficiently penetrate merely by applying the drug to the body surface. In particular, an efficiency of percutaneously absorbing a high-molecular-weight drug is extremely low, and it is difficult to exert effects only by absorption from the skin. Fucoidan is an acidic polysaccharide polymer, its percutaneous absorbability is extremely low, and only a minute amount thereof is absorbed through pores.

Thus, the oral administration method and the application method have a problem of inefficient drug use.

On the other hand, the application method can remarkably improve the efficiency of penetrating the drug by perforating a corneum using a minute needle i.e. a microneedle.

An item in which a lot of the microneedles are accumulated on a substrate is called a microneedle array. In addition, a product which is made easier to use by adding an adhesive tape for attaching the microneedle array to a skin, a covering sheet for keeping a sterile state until use, and the like to the microneedle array, is called a microneedle patch. Herein, the tape refers to a film, cloth or paper coated with an adhesive.

Although many attempts have already been made to transdermally administer a drug using such a microneedle, its use as a hair-growing agent seems not to have yet been reported.

The microneedle can be prepared using a water-insoluble material such as stainless steel and polylactic acid, but a microneedle made of a base (biosoluble polymer base) which dissolves by water in a body such as carbohydrate as a substrate can facilitate intradermal and subcutaneous administration of a drug by previously blending the drug into the microneedle, because the injected microneedle dissolves in the body. Herein, the substrate refers to a main component constituting the microneedle.

The microneedle array made of the biosoluble polymer substance is often manufactured using a mold. A microneedle pattern is formed by lithography using a photosensitive resin, followed by transferring, to prepare a mold having recesses for forming microneedles. A microneedle material is cast on this mold, subsequently heated to evaporate moisture, and then the solidified material is released from the mold to obtain a microneedle array.

PRIOR ART DOCUMENTS

Patent Documents

Patent Document 1: Japanese Patent Application Laid-Open No. 2003-155218
Patent Document 2: Re-publication of WO 01/039731
Patent Document 3: Japanese Patent Application Laid-Open No. 2005-281277
Patent Document 4: Japanese Patent Application Laid-Open No. 2007-262036
Patent Document 5: Japanese Patent Application Laid-Open No. 2008-169140
Patent Document 6; Japanese Patent Application Laid-Open No. 2009-114170
Patent Document 7: Japanese Patent Application Laid-Open No. 2014-218440

SUMMARY OF INVENTION

Problem to be Solved

In a hair root area inside a scalp, there are hair bulbs distributed in the dermic layer having a thickness of 0.5 to 1.5 mm, and hair grows by hair matrix cells inside the hair bulbs. Although a hair-growing agent should be delivered to the dermic layer, its skin penetration is prevented by a corneum barrier, and this is why there are few commonly-effective percutaneous hair-growing agents. The object of the present invention is to develop a novel administration method of the fucoidan-containing hair-growing agent and to provide a means for exerting excellent effects of fucoidan.

Solution to Problem

The present inventors have continued examinations with hope for the administration through the microneedles exerting a hair-growing effect far superior to that of the conventional liquid administration, and this examinations have led to the present invention. The hair-growing agent according to the present invention made in order to solve the above problems is characteristically obtained by combining a fucoidan-containing microneedle and a fucoidan-containing liniment.

In the present invention, it was found that although administration of fucoidan is effective even by administering the fucoidan-containing microneedle alone, the effect is further enhanced by combining the fucoidan-containing microneedle with a fucoidan-containing liquid (essence). Even only the fucoidan-containing microneedle expresses a hair-growing effect far superior to that in application of the fucoidan-containing essence to skin. Furthermore, concomitant use (combination) of both expresses a more excellent effect, which is a feature of the present invention. Although the mechanism remains unclear, it is considered that the mechanism is attributed to the percutaneous penetration of fucoidan contained in the microneedles through skin pores formed by the microneedles, and furthermore to the enhanced intradermal penetration of fucoidan contained in the liquid.

That is, the hair-growing method of the present invention is characterized in that the hair-growing effect is enhanced by combining administration of the fucoidan-containing microneedles and administration of the fucoidan-containing microneedles and fucoidan-containing liquid. As for the timing of concomitant use, the microneedles and the liquid may be simultaneously administered, or each of them may be administered at another time.

The length of the fucoidan-containing microneedle is suitably 0.1 to 1.5 mm. A more suitable length is 0.15 to 1.0 mm. If the length is 0.1 mm or less, the function as a microneedle cannot be sufficiently exhibited. If the length is 1.0 mm or more, the effect is sufficient, but pain due to administration is accompanied, causing problems on a user's compliance. As a base for the microneedle containing fucoidan, a water-soluble polymer is desirable. A biosoluble polymer such as hyaluronic acid, collagen, hydroxypropyl cellulose and chondroitin sulfate is particularly preferred, because skin moisture diffuses in the needle part within a short period after its insertion and the needle part inserted into the skin swells and then dissolves.

As a fucoidan-containing liniment, not only the liquid but also a cream, a mousse, a gel, etc. can be used in combination with a microneedle method. The amount of fucoidan blended in the hair-growing agent varies depending on the dosage form, administration method, desired effect, treatment period, etc. and so cannot be unconditionally defined. However, it is appropriate that its concentration in the liquid or the cream is typically 0.1 µg/mL, to 100 mg/mL. Additionally, in the microneedle preparation, one dose is blended into one or several microneedle arrays, and the dose is suitably 0.1 µg to 2 mg per one microneedle array.

In the hair-growing agent, other hair-growing promoters can be added in order to complement or enhance its hair-growing activity. For example, minoxidil, carpronium chloride, t-flavanone, adenosine, 6-benzylaminopurine, pentadecanoic acid glyceride, crude drug extract and the like are suitable.

In addition to the hair-growing promoter, if necessary, a plant extract, an aqueous component, a moisturizer, a thickener, a preservative, an antioxidant, a perfume, a coloring material, a drug and the like which are approved as a drug, a cosmetic, a quasi drug, a pharmaceutical and the like may be appropriately blended into the hair-growing agent, as long as the purpose and the effect of the hair-growing agent are not impaired.

The plant extract includes red pepper, aloe, tea leaf, magnolia flower, Japanese horseradish, *Ligustrum lucidum* fruit, *Spilanthes acmella*, gardenia, *Asiasarum sieboldii*, garlic, mint, coix seed, *Daemonorops draco*, burdock, licorice, *Gynostemma pentaphyllum, Ganoderma lucidum*, rehmannia root, monoammonium glycyrrhizinate, glycyrrhetinic acid, glycyrrhizin, sesame, cnidium rhizome, polygonum root, rumex root, carrot, ginger tincture and the like, and each of them can be used alone or in combination of plural kinds.

Effects of Invention

The fucoidan-containing microneedle of the present invention can exert a greater effect than in a case of using the conventional liniment alone.

Furthermore, by combining the fucoidan-containing microneedle administration and the fucoidan-containing liniment administration, the hair-growing effect can be greater than in a case of using either one of them alone.

The hair-growing agent of the present invention can be used as any preparation which is widely usable for pharmaceuticals, quasi-drugs, cosmetics and the like.

BRIEF DESCRIPTION OF DRAWINGS

FIG. 1 illustrates a figure showing a method for manufacturing a fucoidan-containing microneedle array.

FIG. 2 illustrates a figure showing comparison of effects of various administration methods for the hair-growing agent of this patent application, and comparison of effects in combination with other hair-growing agents. In the figure, the ordinate represents an amount of the grown hair (mg/cm$^2$).

FIG. 3A illustrates a photograph of a head showing a hair-growing effect of a panelist in hair growth test 3.

FIG. 3B illustrates a photograph of a head showing a hair-growing effect of another panelist in hair growth test 3.

FIG. 4 illustrates graphs showing a questionnaire result regarding use of the hair-growing agent on the panelists after completion of hair growth test 3.

FIG. 5 illustrates graphs showing evaluations regarding hair restoration and hair loss on the panelists after completion of hair growth test 3.

FIG. 6 illustrates a graph showing effects perceived by the panelists after completion of hair growth test 3.

DESCRIPTION OF EMBODIMENTS

Hereinafter, embodiments of the present invention will be explained on the basis of Examples. However, the present invention is not limited to the contents of Examples.

As fucoidan of the present invention, a product purified from *Cladosiphon okamuranus* was used. For this product, a commercial product (LIMUVEIL, made by TANGLEWOOD K.K.) can be used.

(Hair Growth Test 1)

A microneedle pattern having a predetermined shape was formed as shown in FIG. 1 by a lithography method of irradiating a photosensitive resin with light. This microneedle pattern was electroformed to form a mold 10 having microneedle-forming recesses 11 onto which the pattern had been transferred. The microneedle-forming recesses 11 have a stratovolcano shape with a root diameter of 200 μm and a depth of 300 μm, arranged in a lattice pattern at an interval of 600 and 280 recesses are formed per 1 cm². A microneedle array 12 was molded using the recessed mold for formation of the present invention.

5 g of hyaluronic acid (FCH-80, derived from culture, made by Kikkoman Biochemifa Company) and 5 g of LIMUVEIL NV (aqueous solution containing 1.2% of fucoidan, made by TANGLEWOOD K.K.) were added to 90 g of water to prepare a homogeneous solution. The aqueous solution was cast on the mold 10, dried at room temperature for 24 hours, and released from the mold to obtain a microneedle array sheet. This sheet was cut to obtain a microneedle array having a diameter of 1 cm. A content of fucoidan per one microneedle array was 25 μg.

0.1 g of LIMUVEIL HV was dissolved in 200 g of water to prepare a fucoidan-containing extract.

The following animal experiment was carried out in an animal test laboratory of Kyoto Pharmaceutical University in compliance with the operative provision for animal experiment in Kyoto Pharmaceutical University (rule of Kyoto Pharmaceutical University in consideration of viewpoints of science, animal welfare and environmental conservation, and health and safety of persons engaged in animal experiment and the like, on the basis of basic guideline on implementation of animal experiment and the like at research institutes and the like (Public Notice of the Ministry of Education, Sports, Culture, Science and Technology No. 71, in 2006)).

Male C3H/HeN mice (CHARLES RIVER LABORATORIES JAPAN, INC.) were preliminarily raised, and at 6 weeks of age, their backs were sheared by a hair-clipper, and furthermore shaved with a razor for using the mice in the experiment.

A fucoidan-containing microneedle (fMN) and a fucoidan-containing extract (fEX) were administered at a predetermined time interval for 22 days, and after 24 days, an amount of grown hair was measured.

In relation to the single dose, in the case of the microneedle, one patch is applied, and in the case of the inclusion-type extract, 50 μL of the extract was applied on an area of about 1 cm². In both cases, the amounts of fucoidan were the same, 25 μg. The results are summarized in Table 1. From Table 1, it can be found that the concomitant use of the fucoidan-containing microneedle and the fucoidan-containing extract is excellent in hair-growing effect.

In the hair growth test, the alternate-day administration refers to an aspect that the fMN was administered on the first day and the fEX was administered on the next day, and this cycle of the fMN and fEX was continued 11 times for 22 days. The administration of 2 days out of 3 days refers to an aspect that the fMN was administered on the first day, the fEX was administered on the second day and administration was suspended on the third day, and this cycle was continued 8 times for 23 days. Note that, when the hair-growing agent to be administered was one kind, the agent was administered on the first and second days, and administration was suspended on the third day, and this cycle was repeated 8 times (16 applications), which refers to administration continued for a total of 23 days.

TABLE 1

Hair growth test result

| test number | administered hair-growing agent | interval of administration | amount of the grown hair |
|---|---|---|---|
| Example 1 | fMN + fEX | alternate-day | 0.7 |
| Example 2 | fMN + fEX | 2 days out of 3 days | 0.6 |
| Comparative Example 1 | fMN | 2 days out of 3 days | 0.3 |
| Comparative Example 2 | fEX | 2 days out of 3 days | 0.1 |
| Comparative Example 3 | not administered | | 0 |
| Reference Example 1 | commercial product | alternate-day | 0.2 |

A unit of the amount of the grown hair is mg/cm².

The commercial product in the Reference Example is a 5% minoxidil aqueous solution (Taisho Pharmaceutical Co., Ltd.).

(Hair Growth Test 2)

The hair-growing effects were compared using fucoidan-containing extract as a main active ingredient in various administration methods. In the same manner as in the hair growth test 1, C3H/HeN mice were sheared and shaved.

The administered drugs and administration methods are summarized in Table 2. After 40 days, grown hair was shaved off, washed, dried, and its weight was measured in order to quantitate the hair growth state.

The administered drug was somewhat different from that in the hair growth test 1. The microneedle array (MN) was not blended with only 5 g of LIMUVEIL HV in the hair growth test 1, but 1 g of carrot extract (MARUZEN PHARMACEUTICALS CO., LTD.) and 1 g of ginger tincture (MARUZEN PHARMACEUTICALS CO., LTD.) were added to 5 g of LIMUVEIL HV. The method of manufacturing the microneedle array is the same as in the hair growth test 1.

As a liniment, a LIMUVEIL liquid (LQ) was used. A fucoidan content therein did not correspond to 0.1 g of LIMUVEIL HV in the hair growth test 1, but corresponded to 0.02 g of carrot extract (MARUZEN PHARMACEUTICALS CO., LTD.) and 0.02 g of ginger tincture (MARUZEN PHARMACEUTICALS CO., LTD.) in addition to 0.1 g of LIMUVEIL HV, and the production method for the liniment was exactly the same as in the test 1.

For both MN and LQ, the doses were 25 μg in terms of fucoidan. For the reference example (commercial product), a 5% minoxidil aqueous solution (RiUP) (X) was used, and its dose was 40 μL.

The administration cycle of each preparation in the hair growth test is shown in Table 2, and the result of the amount of the grown hair 40 days after administration is shown in FIG. 2. A unit of the amount of the grown hair is mg/cm².

TABLE 2

| aspect | \multicolumn{13}{c}{Administration schedule - day} |
|---|---|---|---|---|---|---|---|---|---|---|---|---|---|

| aspect | 1 | 2 | 3 | 4 | 5 | 6 | 7 | 8 | 9 | 10 | 11 | 12 | 13 |
|---|---|---|---|---|---|---|---|---|---|---|---|---|---|
| only LQ (1) | LQ |  | LQ |  | LQ |  |  | LQ |  | LQ |  | LQ |  |
| only MN (1) | MN |  | MN |  | MN |  |  | MN |  | MN |  | MN |  |
| only LQ (2) | LQ | LQ | LQ | LQ | LQ | LQ | LQ | LQ | LQ | LQ | LQ | LQ | LQ |
| only MN (2) | MN | MN | MN | MN | MN | MN | MN | MN | MN | MN | MN | MN | MN |
| LQ + MN (1) | MN | MN | LQ | MN | MN | LQ | MN | MN |  |  | MN | MN | LQ |
| LQ + MN (2) | MN | LQ | MN | LQ | MN | LQ | MN | LQ | MN | LQ | MN | LQ |  |
| LQ + MN (3) | MN | LQ | LQ | MN | LQ | LQ | MN | LQ | LQ | MN | LQ | LQ |  |
| commercial product | X |  | X |  | X |  |  | X |  | X |  | X |  |

From the results in Table 2 and FIG. 2, it was found that it was extremely effective to alternately administrate the microneedle and the liquid as the administration method of fucoidan. In relation to the administration program, it could be confirmed that the fucoidan-containing extract was optimal as the main valuable component, and concomitant administration of the microneedle application and the liquid was more effective.

(Hair Growth Test 3)

Volunteers were tested at a specialized agency where efficacies of cosmetics and quasi drugs were evaluated. Informed consent was obtained from each volunteer subject, and various tests were implemented. The outline of the implementation was as follows.

1. Panelists: 4 males (48 to 57 years old), 8 females (47 to 59 years old)
2. Test period: 12 weeks
3. How to use
   The hair-growing needle and the hair-growing liniment were the same as those used in Example 2.
   Number of applications of the hair-growing needle: 3 times/week
   Number of applications of the hair-growing liniment: morning/night use
4. Evaluation of effect The effect was judged by head photographs between before and 12 weeks after the use. Two representative examples out of 12 subjects are shown. After 12 weeks, in the heads of the two panelists, increase of hair around the area on which the hair-growing needle had been pasted was remarkably observed with the naked eye (FIGS. 3A and 3B).

Evaluation results and questionnaire results of 12 panelists are shown (FIGS. 4 to 6). In relation to the use of the hair-growing agent of the present invention, two-thirds of panelists were satisfied, and 80% or more of panelists indicated willingness to continue to use it (FIG. 4). In relation to the decrease of hair loss and increase of hair, the majority of panelists perceived its effect (FIG. 5), and it is considered that the panelists who perceived the effect and the panelists who expect future effects expressed their intention to continue the use. Moreover, in addition to the decrease of hair loss and the hair growth, effects such as increased hair thickness, volume-up of hair, increased firmness and resilience of hair and decreased white hair are also perceived, and it was found that 87% of the panelists perceived any advantageous effect for hair (FIG. 6). 13% of panelists answered that there was no effect, but no adverse effect on hair was observed.

The invention claimed is:

1. A hair-growing method comprising alternately administering one or more doses of a fucoidan-containing microneedle array and one or more doses of a fucoidan-containing liniment to a skin of a subject in need thereof,
   wherein the fucoidan in the fucoidan-containing microneedle array is present at a dose of 0.1 µg to 2 mg per one fucoidan-containing microneedle array and the fucoidan in the fucoidan-containing liniment is present at a concentration of 0.1 µg/mL to 100 mg/mL.

2. The hair-growing method according to claim 1, wherein a base of the fucoidan-containing microneedle array is a biosoluble polymer.

3. The hair-growing method according to claim 1, wherein the fucoidan in the fucoidan-containing microneedle array and the fucoidan-containing liniment is derived from a brown alga.

4. The hair-growing method according to claim 1, wherein the fucoidan-containing microneedle array and/or the fucoidan-containing liniment further comprise a hair-growing promoter selected from the group consisting of minoxidil, carpronium chloride, t-flavanone, adenosine, 6-benzylaminopurine, pentadecanoic acid glyceride, and crude drug extract.

5. The hair-growing method according to claim 1, wherein the fucoidan-containing microneedle array and/or the fucoidan-containing liniment further comprise one or plural kinds of plant extracts selected from the group consisting of red pepper, aloe, tea leaf, magnolia flower, Japanese horseradish, *Ligustrum lucidum* fruit, *Spilanthes acmella*, gardenia, *Asiasarum sieboldii*, garlic, mint, coix seed, *Daemonorops draco*, burdock, licorice, *Gynostemma pentaphylium*, *Ganoderma lucidum*, rehmannia root, monoammonium glycyrrhizinate, glycyrrhetinic acid, glycyrrhizin, sesame, cnidium rhizome, polygonum root, rumex root, carrot, and ginger tincture.

6. The hair-growing method according to claim 5, wherein the plant extracts are a carrot extract and a ginger tincture.

* * * * *